United States Patent
Nix et al.

[11] Patent Number: 6,011,391
[45] Date of Patent: Jan. 4, 2000

[54] PROBE FOR MEASURING THIN LAYERS USING A MAGNETIC OR EDDY CURRENT PROCESS

[75] Inventors: Hans F. Nix, Köln; Gang Zhang, Wuppertal, both of Germany

[73] Assignees: Elektro-Physik Hans Nix; E. Steingroever GmbH & Co KG, both of Köln, Germany

[21] Appl. No.: 08/922,479

[22] Filed: Sep. 3, 1997

[30] Foreign Application Priority Data

Sep. 4, 1996 [DE] Germany ............................ 196 35 853
Aug. 15, 1997 [DE] Germany ............................ 197 35 433

[51] Int. Cl.[7] ................................ G01B 7/10; G01B 5/06
[52] U.S. Cl. ............................................ 324/230; 33/834
[58] Field of Search ................................. 324/229, 230, 324/231, 226, 236–241; 33/834

[56] References Cited

U.S. PATENT DOCUMENTS

| 5,006,799 | 4/1991 | Pfanstiehl ............................. | 324/230 |
| 5,053,703 | 10/1991 | Fischer .................................. | 324/230 |
| 5,525,903 | 6/1996 | Mandl et al. ........................ | 324/230 |

FOREIGN PATENT DOCUMENTS

| 36 22 708 A1 | 1/1988 | Germany . |
| 39 02 095 A1 | 7/1990 | Germany . |
| 637471 | 8/1990 | Germany . |

*Primary Examiner*—Jay M. Patidar
*Attorney, Agent, or Firm*—Fisher, Christen & Sabol

[57] ABSTRACT

Measurement probe (1) is used for measuring thin layers (19) on base material (20) using a magnetic or eddy current process. On probe housing (5) above a stop for guide means (3) with measurement sensor (12) and measurement pole (13) sliding element (2) for measurement sensor (12) is guided to move in the longitudinal axis of probe housing (5) as limited by a stop. Between sliding element (2) and stop (9) on guide means (3) there is first helical spring (4) by which sliding element (2) is elastically supported relative to measurement sensor (12). Between stop (9) on guide tube (3) and lower abutment (30) on probe housing (5) is second helical spring (10) which interacts with first helical spring (4) and elastically supports measurement sensor (12) in the rest state at a distance above opening (5a) for measurement pole (13) in probe housing (5). By means of the elastic arrangement of the guide means with the measurement sensor in the probe housing between the interacting helical springs a very small load pressure of the measurement pole on the layer to be measured is achieved with the measurement sensor lowered. When measuring with the invention measurement probe, first the probe body with the probe foot is seated on the layer to be measured. Only then is the measurement sensor slowly placed on the surface by actuating the sliding element, in a damping and elastic manner. The measurement sensor withdrawn into the interior of the probe body is held in the relieved unused state of the probe and does not project above the seating surface of the probe foot.

40 Claims, 3 Drawing Sheets

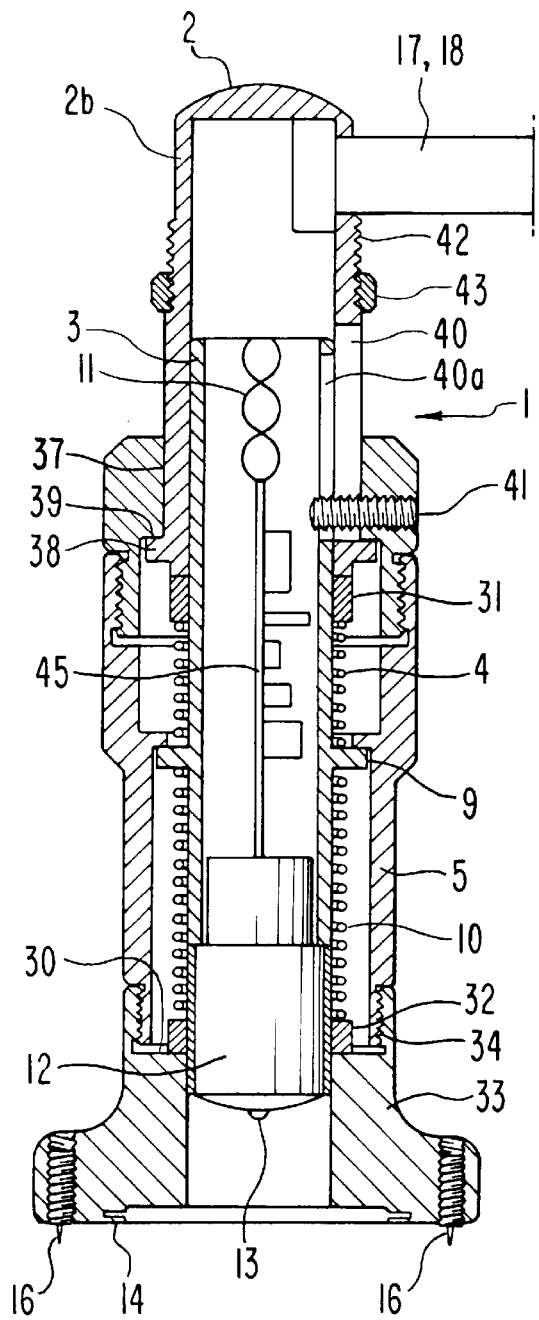
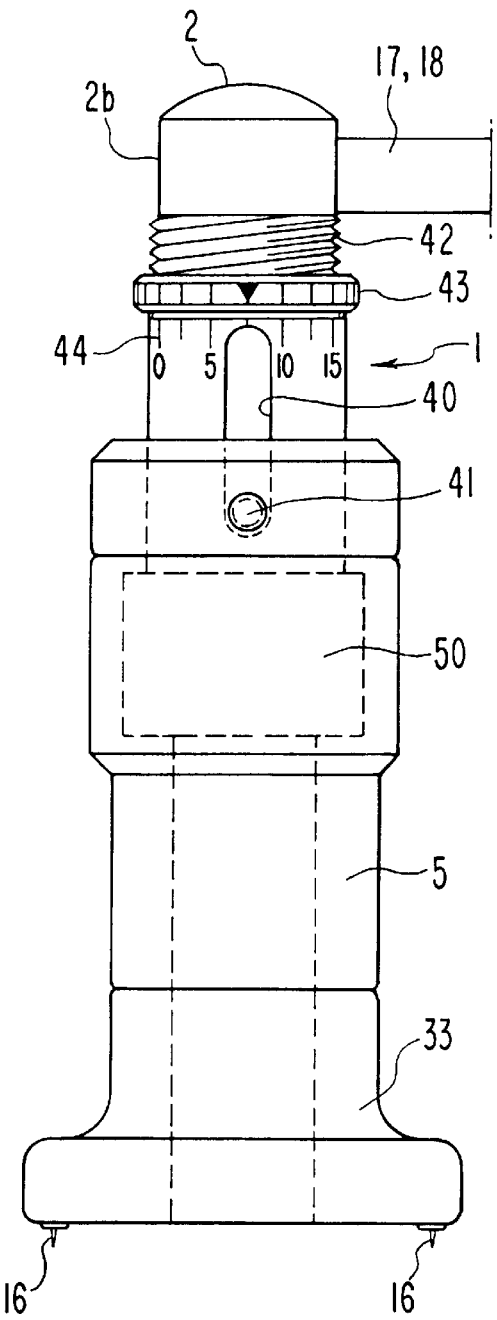

PROBE FOR MEASURING THIN LAYERS USING A MAGNETIC OR EDDY CURRENT PROCESS

BACKGROUND OF THE INVENTION

1. Field of the Invention

The invention relates to a probe for measuring thin layers on a base material using a magnetic or eddy current process.

2. Background Art

In nondestructive measurement of the thickness of solid layers such as enamels, galvanic layers and the like, on generally metallic base materials, or in the measurement of the thickness of films such as plastic films which have been applied to a metallic base material, layer thickness measuring instruments which exploit a magnetic or eddy current process are used. In these measuring instruments the measurement pole of the measurement sensor is made spherical with a radius of curvature of typically 1 to 10 mm. The measurement sensor with the spherical measurement pole is placed either directly by hand on the surface of the layer to be measured, or the measurement pole is under the action of a pretensioned spring which is located in the holder of the measurement sensor, with a specific load pressure on the layer to be measured. When the measurement probe is placed directly, the load pressure depends on the weight of the hand and can be from a few tenths of a Newton to a few dozen Newtons.

When measuring solid layers the differing load pressure of the measurement pole is of secondary importance. When measuring powdery or soft layers on a solid base material or layers on an elastic base material, however, various disadvantages arise.

When the measurement pole with a pretensioned spring is placed in the probe holder, the load pressure of the measurement pole is constant and is typically 0.5 to 1 Newton.

The disadvantage of this type of probe for the measurement of powdery or soft layers, but also thin layers especially on elastic base materials is however that the load pressure when using typical radii of curvature of 1 to 10 mm of the spherical measurement pole exerts such a great compressive effect on the surface that for example a powdery or soft layer is punctured or the measurement pole penetrates at least strongly and to various depths into the layer material.

For elastic base materials deformation of the measured article can be caused by the compressive effect. The result is incorrect measured values.

This danger also exists when the measurement sensor is lowered by hand. The mass inertia of the measurement sensor leads to a considerable force acting on the layer when the measurement pole is placed on the surface, even if it weighs only a few grams, as a result of the abrupt deceleration of the hand from roughly 10 to 20 cm/s to 0 cm/s within a path length of only a few microns, so that the measurement pole can penetrate as far as the base material especially for powdery or soft layers or the layer can be indented at least to a considerable degree. The mass forces are between 0.2 to 20 Newton when the probe is placed by hand.

The mass forces during measurements act similarly on pliable materials of the measurement article.

A reproducible measurement when using typical known probes is, therefore, not possible on powdery or soft layers or on measured articles with pliable materials at these high and varied forces. Practice confirms this statement. Depending on how the probe is placed, the measured values decrease by few percent or to zero percent of the original layer thickness. The measurement result is therefore essentially useless. For this reason contact layer thickness measurement probes are not used in particular for measuring powdery and soft layers.

The same applies to measurements on articles with pliable materials.

In practice there is also the urgent desire to determine the thickness of still powdery or soft layers before firing or hardening in order to be able to make a correction as quickly as possible before the next working process.

At present the correction can be made only after measuring the solid layer, therefore after firing or hardening, since commercial measuring devices are only able to measure solid layers. The waiting time, for example, in a powder coating, between application of the powder layer and the earliest possibility of layer thickness measurement of the fired layer is roughly one hour; this is a time interval which is very uneconomical if the deviations of layer thickness must be corrected.

One example of layers to be measured are also thin enameled layers on metal foils, for example, internally enameled aluminum tubes for toothpastes and similar mixtures. Conventional hand measurement probes bend the thin base material when the measurement pole is placed and, therefore, do not deliver reproducible results.

German Published Patent Application No. 3,622,708 A1 discloses a measurement probe which is used to test final paint jobs on motor vehicle chassis. This measurement probe is gimbaled and guided lengthwise on the chassis by means of automatic handling machinery. It is placed vertically on the surface to be measured by the automatic handling devices with a certain contact pressure. By pretensioning of a compression spring which supports the measurement probe the full pretensioning force of this compression spring takes effect after contact of the probe pole with the surface to be measured. During the measurement the measurement probe is held by a suction cup on the chassis.

To lift the probe system off the chassis air must be introduced again into the suction cup via the suction line. In this way the vacuum of the suction cup is canceled, by which the suction cup is lifted off of the surface of the chassis. It is not possible to place the measurement probe on the same measurement point with pinpoint accuracy again and check the first measurement.

Another layer thickness measurement probe is known from British Patent No. 637,471. This measurement probe uses the electromagnetic adhesive force principle. The holding force of the pole pin which acts on the surface of the coated soft-magnetic steel base material derives from the interaction of an armature spring with low spring force and the electromagnetic force of the coil system which is supplied with direct current of a battery. The adhesive force is indirectly measured by the exciter current flowing through the coil. The measured quantity is the current measured on an ammeter which, by continuous reduction starting from a maximum current, is no longer enough to hold the pole pin against the compressive force of the armature spring on the layer surface. When the pole pin is removed from the surface to be measured, a contact is closed which causes a lamp to illuminate after the switch is turned on. At this instant, further reduction of the current must be stopped using two resistors since this current value is a measure of layer thickness.

Another measure of layer thickness is the spring force of the armature spring which acts as a measurement spring together with the electromagnetic adhesive force of the pole pin. Diminution of the spring force, for example, by aging, changes the deflection of the ammeter and thus also the layer thickness display. In this measurement device the slackening of the armature spring would lead to a smaller layer thickness display than that of the actual layer thickness.

In the known device there is also a second larger spring which however does not act on the pole pin and, thus, has no effect on the load pressure of the pole pin on the layer surface. In addition, the electromagnetic adhesive force in this measurement probe depends very heavily on the layer thickness, so that as a result of the measurement principle strong different load pressures must arise. A constant contact force or almost zero load pressure is not possible due to the electromagnetic adhesive force principle in this known measurement probe. If the two contacts for the display light are closed, the pole of the pole pin can be pressed with any strength against the surface by exerting variously intense pressure on the measurement probe. This known measurement probe, therefore, does not enable usable measurement results for thin, powdery or soft laminated materials.

German Published Patent Application No. 3,902,095 A1 discloses another measurement probe for measuring thin layers on electrically conductive base materials. When the probe is placed, a sliding sleeve touches the measured article. Since the probe, however, is held by hand on the outer grip sleeve, this grip sleeve slides down in the direction of the measured article in one motion. In doing so the probe body is moved down via two stops against the action of a helical spring. This helical spring, however, is designed only to press back the probe body in the rest state into the sliding sleeve or to elastically oppose the probe body with a sensor part supported in leaf springs after placing the sliding sleeve, until the spherical surface of a cup core which forms the measurement pole sits on the surface of the measured article. Softly setting the spherical surface of the measurement sensor in this known measurement probe is only possible within the framework of the stipulated small spring path of the two stationary-mounted leaf springs and, thus, only within narrow limits. In this known measurement probe, as a result of the short spring paths, relief of the spring system is not possible, by which also it becomes impossible to place the sensor system again with pinpoint accuracy for a repeated measurement process at the same location. When the grip sleeve is released, brief lifting of the entire measurement probe from the measurement surface in manual operation cannot be avoided, unless the probe were to be guided in a stand. When the probe is placed again by hand, however, another measurement point is touched in any case. In this known measurement probe the load pressure is fixed by the construction features of the probe and the leaf springs used. Adjustment of a maximum load pressure by the probe operator is not possible. Other load pressures require probes with different construction features.

The load pressure of the measurement sensor is otherwise also dependent on the measurement direction, to the extent that in measurements from top to bottom it is different than in overhead measurements from bottom to top. These difference load pressures are invariable. It is not possible to adapt the spring system depending on the measurement direction.

In the known measurement probe the measurement system is also freely elastically suspended with two leaf springs and can therefore swing freely axially. When the probe is moved between individual measurements and during all handling, however, acceleration and deceleration forces occur which allow the measurement system to continuously push against the stop surfaces inside of the probe. These pushes are disadvantageous for the measurement properties and the measurement accuracy of these precision measurement devices.

Since processes of placement of the sliding sleeve on the measured article and the measurement system with the spherical placement surface of the cup core on the surface to be measured cannot be carried out in separate steps, in this known measurement probe other disadvantages arise. The process of placing the entire probe with its mass and with the mass of the hand and arm of the operator cannot be executed in a controlled manner with respect to placement speed.

In this way the time of contact of the face of the sliding sleeve with the measured article cannot be unambiguously detected by the operator. Softly placing the cup core with minimum transfer of momentum requires immediate braking of the placement process after the first contact of the sliding sleeve, so that the measurement system very slowly touches the surface. But this is not possible in the known measurement probe due to the uncontrolled placement speed which is caused by the different masses of the probe, hand, and arm of the operator.

BROAD DESCRIPTION OF THE INVENTION

The main object of the invention is to reduce the static load pressures and the dynamic forces in the measurement of thin layers with a measurement probe of the initially specified type, such that in spite of contact measurement, as much as possible also of powdery or soft layers, as well as in measurements on articles with pliable materials a reproducible measurement result which delivers reliable values for the individual making the assessment is achieved.

The main object of the invention is achieved by means of a measurement probe for measuring thin layers on a base material using a magnetic or eddy current process with a tubular probe housing with a face-side lower opening for a measurement sensor with a measurement pole which is located on the bottom end of a guide means which is guided to move in the longitudinal axis of the probe housing against spring action as limited by a stop, in the initial position or rest position of the measurement sensor a stop on the guide means interacting with an abutment on the probe housing. This is done by the fact that above the abutment a sliding element for the measurement sensor is guided to move on the probe housing as limited by a stop, and that in the path of the force between the sliding element and the measurement sensor there are two interacting helical springs with differing spring force which are dimensioned such that in the initial position of the measurement sensor the spring force of one helical spring is less than the spring force of the other, such that when the sliding element is actuated first one helical spring is tensioned until its spring force overcomes the opposing force of the other helical spring and in this way the guide means with the measurement sensor is moved first against the action of the other helical spring from the withdrawn rest position into the measurement position; after the latter is reached further pressure on the sliding element is elastically captured by the first helical spring.

By means of the elastic arrangement of the guide means with the measurement sensor in the probe housing between two interacting helical springs with different spring force a very low load pressure of the measurement pole on the layer to be measured is achieved with the measurement sensor lowered.

During measurement with the measurement probe of the invention, first the probe body with its probe foot is placed on the layer to be measured. Only then is the measurement sensor placed slowly and elastically on the surface by actuating the sliding element, such as a grip cap or press pin. In doing so the measurement pole first touches the measured article without force and the load pressure increases linearly from zero to a preselectable low final load pressure by further pressing on the actuating element.

In the released, unused state of the probe the measurement sensor is held withdrawn within the probe body and does not project above the seating surface of the probe foot.

The possibility of a preselectable or adjustable load pressure of the measurement sensor by changing the clamping length of one of the two or both springs of the spring system is especially advantageous; this is done, for example, by adjusting the screwed-on annular stop either in the longitudinal direction of the guide means up or down or by using spacer rings of varied thickness on the ends of the helical springs.

Turning the annular nuts attached to the outside of the measurement probe likewise allows preselectable adjustment of the final load pressure. Especially when using helical tension springs their spring forces and, thus, the final load pressure of the probe system can be easily changed by set screws on one end of the spring.

For measurement purposes the probe foot with its flange-like top seating surface is seated flat on the layer to be measured and acts like a small stand. Therefore, pinpoint repeated measurements can be taken by repeatedly lowering the measurement sensor from the raised rest position into the measurement position at the same location.

Measurement with the probe proceeds as follows:

by actuating the pusher made as a slide element initially the first weaker helical spring is tensioned until its spring force is equal to the pretensioning force of the second stronger helical spring;

as the sliding element continues to be pushed down the measurement sensor moves with its guide means against the layer to be measured, while the spring forces of the two helical springs act continually against one another and essentially cancel one another (except with negligible forces of mass and friction). The measurement sensor thus almost "floats" against the layer.

at the time of contact of the measurement pole with the layer the measurement sensor sits without force on the layer. Further movement of the slide element is then accommodated by the first helical spring.

In the measurement probe of the invention, after seating of the probe body with the probe foot, the measurement sensor is guided from a defined greater distance against the layer to be measured and the load pressure of the measurement pole increases from zero to the preselectable adjusted final pressure after contact of the layer.

Especially accurate mass compensation when the measurement probe is seated on the measured article is achieved according to one development of the invention by the two helical springs being made as tension springs, the weaker tension spring being located between the sliding element and the guide means with the measurement sensor and the other stronger tension spring being located between the guide means and the housing head. The two tension springs can, thus, be located next to one another in an especially space-saving manner in the interior of the guide means parallel to its axis, the weaker tension spring in its upper end being joined to an upper crosspiece on the guide means and with its lower end being attached to an adjustment pin which penetrates the springs to the full length from overhead. On the top end of the adjustment pin sits the sliding element on the housing top. The other stronger tension spring is clamped between a retaining eye in the interior of the guide means above the measurement sensor and an adjustable retaining eye on the housing head. In doing so, easy movement and, thus, the measurement accuracy of the probe can also be improved by the guide means being guided in the probe housing with a ball guide.

It has, furthermore, unexpectedly been shown that by means of an elastically flexible film or foil of a material suitable for measurement engineering, for example, plastic or bronze, which is located between the measurement pole of the measurement sensor and the layer material, the surface pressure on the powdered or soft layer is reduced such that the penetration of the measurement system into the layer can be ignored and reproducible measurement results can be obtained. The pressure reduction film or foil is attached to the measurement probe or to the measurement device with an integrated measurement sensor and is, thus, part of the measurement probe or the measuring device.

It is located between the measurement pole and layer and, thus, increases the radius of curvature of the contact surface of the measurement pole. This reduces the specific load pressure; this leads to higher measurement accuracy especially for very soft and powdered layer material.

To better use the favorable initial characteristic of the measurement sensor when measuring thin layers, the probe foot with the film or foil can be removed from the probe body, for example, by screwing and replaced by another probe foot without film or foil with flat seating locations. The thickness of the film in the evaluation of the measurement results is subtracted so that only the thickness of the layer on the base material is measured.

Here it does not matter whether the absolutely highest thickness is determined. For predetermination of the layer thickness which arises after firing or hardening, it is enough to determine the typical thickness of the powdered or soft layer. This typical thickness, even if it is smaller than the absolutely highest value, is in a fixed empirical relationship to the solid layer which arises after firing or hardening.

A previously unused range of application of these layer thickness measurement instruments is covered by the pressure reduction film or foil additionally applied to the measurement probes with insignificant added cost. The use of measurement probes is also very similar to handling of known measurement probes and devices when using "pressure reduction film or foil", so that the operator need not learn new handling rules.

When using the measurement probe with a pressure reduction film or foil and seating tips on the probe foot the penetration of powdery or soft layers by the seating tips no longer had an adverse effect, since soft layers close again after lifting the probe or the powder layer likewise closes again after firing by melting of the powder. The probe foot acts like a small support. Measurements can be repeated at will when the probe body is seated by releasing and pressing down the actuating element again.

In measurement with the measurement probe the measurement sensor after seating the probe body with the probe foot is guided from a defined greater distance against the layer to be measured and the load pressure of the measurement pole increases from zero to the preselectable adjusted final pressure after contact of the pressure reduction film or foil or the layer to be measured.

The pressure reduction film or foil also has the advantage that little or no powder dust penetrates into the movement mechanism of the layer thickness measurement probe. When powder penetrates, there is uncontrolled friction on the moving parts and this leads to different load pressures which do not enable reproducible measurements. This is counteracted by the pressure reduction film or foil.

The probe foot which can be unscrewed also easily allows the optionally necessary removal of penetrated powder dust from the inner guide surfaces for the measurement sensor by blowing out or using compressed air.

The removable probe foot can also be replaced by a probe foot with an inverted V-shaped notch or groove for measurement on longitudinally arched or cylindrical, also tubular articles.

Preferred embodiments of the invention are shown schematically in the drawings.

BRIEF DESCRIPTION OF THE DRAWINGS

In the drawings:

FIG. 4 shows a longitudinal section through a modified second embodiment of the invention of a measurement probe in which the measurement sensor is moved into the measurement position by pressure on an end-side press pin using the mechanical pencil principle;

FIG. 5 shows an outside view of this second measurement probe;

DETAILED DESCRIPTION OF THE INVENTION

Figure 1:
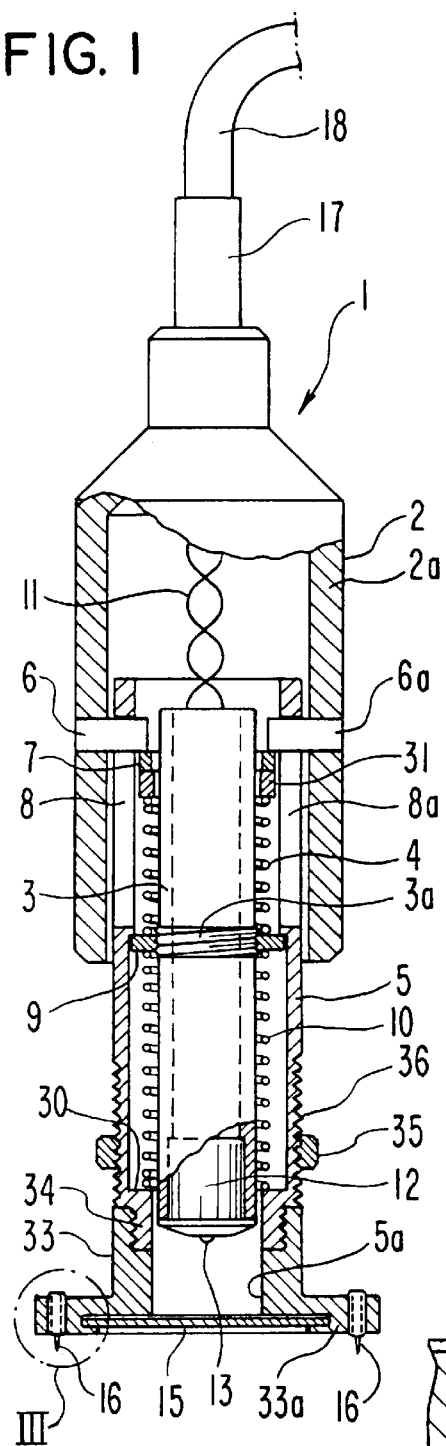
FIG. 1 shows a section through a first embodiment of the invention of a measurement probe in the rest state of the measurement sensor, the measurement sensor being located at a distance above the measurement position.
Figure 2:
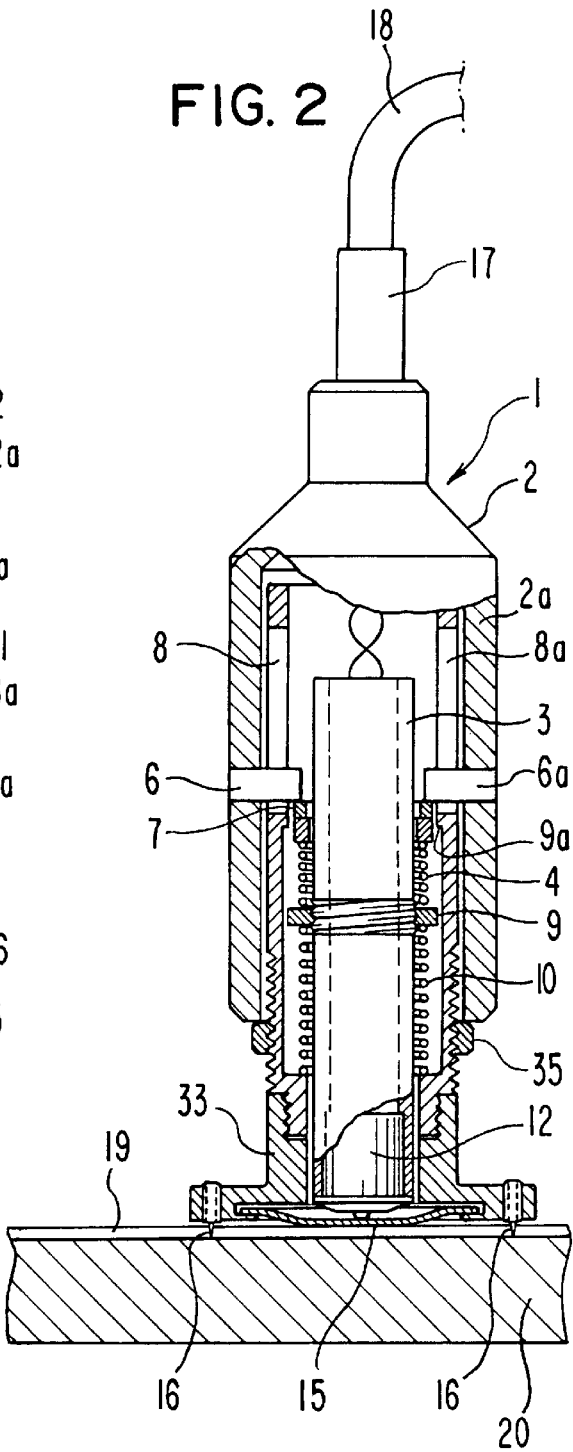
FIG. 2 shows a section through the measurement probe of FIG. 1 in the measurement position in which the measurement sensor with the measurement pole lies on a pressure reduction film or foil for measuring a powdery or soft layer on a solid base material.

In the first embodiment of measurement probe 1 shown in FIGS. 1 and 2, on multi-part cylindrical probe housing 5, grip cap 2a is guided to move lengthwise as a sliding element 2 against the pressure of two helical springs 4 and 10 of different sizes. Two helical springs 4 and 10 are located coaxially to one another on a guide tube as guide means 3 which carries measurement sensor 12 with spherical measurement pole 13 on its lower end. From grip cap 2a two carrier pins 6, 6a are pointed radially to the inside; with them grip cap 2a on probe housing 5 is guided to move lengthwise in guide slots 8, 8a. Carrier pins 6, 6a lie on support ring 7 on the top end of helical spring 4 for lowering measurement sensor 12 with measurement pole 13 from the rest position shown in FIG. 1, in which the measurement pole is located in a raised position at a greater defined distance from layer 19 to be measured, into the measurement position from FIG. 2. Layer 19 is located on base material 20.

As can be seen in particular in FIGS. 1 and 2, measurement probe 1 has tubular probe housing 5 with face-side lower opening 5a for measurement sensor 12 with measurement pole 13.

Measurement sensor 12 located on the lower end of guide means 3 is guided with the guide tube in the longitudinal axis of probe housing 5 against spring action as limited by a stop.

Annular stop 9 on the guide tube interacts with annular abutment 9a on probe housing 5.

On probe housing 5, above abutment 9a for stop 9 of guide means 3, pusher 2 for measurement sensor 12 is guided to move in the longitudinal axis of probe housing 5 likewise as limited by a stop. Pusher 2 can be grip cap 2a (FIGS. 1 and 2) or press pin 2b (FIGS. 4 and 5).

Between the pusher or slide element 2 and stop 9, on guide means 3 is first helical spring 4 which is made as a compression spring and by which the pusher is elastically supported relative to measurement sensor 12.

Between stop 9 on the guide tube and lower annular abutment 30 on probe housing 5 there is moreover second helical spring 10 which is likewise made as a compression spring and acts against first helical spring 4. Measurement sensor 12 is elastically supported in the rest state from FIG. 1 at a distance above opening 5a for measurement pole 13 in probe housing 5.

The spring force of first helical compression spring 4 in the initial position in which stop 9 abuts abutment 9a is less than the spring force of second helical compression spring 10 such that when pusher 2 is pressed down first of all first helical spring 4 is compressed until its spring force overcomes the counterforce of second helical spring 10 and, thus, guide means 3 is moved with measurement sensor 12 against the action of second helical spring 10 from the withdrawn rest position into the measurement position of FIG. 2. After reaching the measurement position further pressure on pusher 2 is elastically captured by the first helical compression spring.

Stop 9 for two helical compression springs 4, 10 is axially adjustable on guide means 3. It is advantageously made as an annular nut adjustable on the guide tube in thread 3a.

On the guide tube, on the ends of helical springs 4, 10 there can be one or more spacer rings 31, 32 for setting the final load pressure of measurement pole 13 on layer 19 to be measured.

Probe housing 5 has probe foot 33 which is flared in the manner of a flange around opening 5a for measurement sensor 12. This probe foot 33 is detachably joined to the lower part of probe housing 5 by means of screw thread 34 or a quarter-turn connection. Probe foot 33 consists of transparent acrylic glass.

In the first embodiment shown in FIGS. 1 and 2, sliding element 2 for measurement sensor 12 is made as cylindrical grip cap 2a which extends over the top end of probe housing 5, with two carrier pins 6, 6a which are pointed radially to the inside and which are guided in longitudinal slots 8, 8a parallel opposite one another on probe housing 5 on either side of guide means 3 as limited by stops, and rest with their free ends on support ring 7 as the upper abutment for first helical spring 4.

On probe housing 5 there is axially adjustable annular nut 35 as the lower end stop for grip cap 2a. This annular nut 35 can be adjusted in thread 36 as required.

In the second embodiment of the invention, measurement probe 1 shown in FIGS. 4 and 5, sliding element 2 for measurement sensor 12 is made as tubular press pin 2b. This press pin 2b is arranged to move in the manner of a telescope and limited by a stop on the top end of guide means 3 and, moreover, in concentric opening 37 on the top end of probe housing 5. With its lower annular end it is used as an abutment for upper helical spring 4, in FIG. 4 spacer ring 31 for changing the spring force being located on the top end of helical spring 4.

Press pin 2b on the bottom end has annular flange 38 with which it is axially supported on inner recess 39 on the top end of probe housing 5. In addition, press pin 2b has longitudinal slot 40 and the guide tube has longitudinal slot 40a for stud 41 which projects to the inside from probe housing 5 for locking purposes.

In addition, on press pin 2b there is annular nut 43 which is adjustable on thread 42 with scale 44 for preselectable adjustment of the final load pressure on the measurement article by limiting the path when actuation element or pusher 2 is pressed down.

In this second embodiment, on the ends of two helical springs 4, 10 are spacer rings 31, 32 for adjusting the spring forces of the two helical springs which act against one another.

In the two embodiments shown, on the upper end of measurement probe 1 probe cable 18 proceeds from grip cap 2a or press pin 2b. The cable is provided with antikink measures 17 and on the inside of measurement probe 1 by means of flexible lead wires 11 it is joined to circuit board 45 (FIG. 4) which is located within guide means 3 for measurement sensor 12 and which is connected to measurement sensor 12.

Two measurement probes 1 can be used in the above described embodiment for measuring solid layers 19 on solid base materials 20. Probe foot 33 rests with its flat even bottom 33a on the layer to be measured, measurement sensor 12 in probe housing 5 first assuming the rest position shown in FIGS. 1 and 4 at a more or less great distance from layer 19 to be measured, from which it is lowered for each measurement process by means of sliding element 2, grip cap 2a or press pin 2b into the measurement position from FIG. 2.

In order to be able to use measurement probe 1 for measuring powdery or soft layers 19 on solid base materials 20 or those which are also of limited pliability, on probe foot 33 around opening 5a for measurement sensor 12 there are screw-in openings for at least three seating tips 16.

Moreover, in opening 5a for measurement sensor 12 film or foil 15 for pressure reduction is attached to probe foot 33. The film or foil consists of elastic, dimensionally stable material such as plastic or bronze, of such a composition that powdery materials for the most part do not adhere to it. It is inserted in the manner of a membrane on its periphery in annular groove 14 on probe foot 33 and preferably has a corrugated external area similar to a speaker membrane.

As is shown by the broken line in FIG. 5, in the two embodiments between sliding element 2 and measurement sensor 12 there can be pneumatic or hydraulic damping system 50 which, regardless of the actuation speed, for the most part allows measurement sensor 12 to be lowered by hand with a uniform, but slow speed against film or foil 15 or onto layer 19 to be measured.

FIGS. 1 and 2 show how layer thickness measurement probe 1 works. In FIG. 1 measurement sensor 12 attached to guide means 3 is pushed into probe housing 5 and is kept in the stop position shown by helical springs 10. Measurement pole 13 does not touch film or foil 15. Film or foil 15 is, therefore, relieved and is located loosely in annular groove 14.

In FIG. 2 the measurement probe is shown in the measurement position. For measurement purposes probe housing 5 is seated with three seating tips 16 on base material 20 with powdery or soft layer 19 to be measured. Afterwards grip cap 2a is pushed slowly downward by hand against the pressure of helical spring 4. Carrier pins 6 and 6a attached in grip cap 2a thus press springs 4 together via support or carrier ring 7 until the pretensioning force of second helical spring 10 which surrounds the guide tube with measurement sensor 12 has been overcome and measurement sensor 12 with measurement pole 13 comes to rest with a delay on film 15 and presses it with a defined small force against layer 19.

In doing so measurement pole 13 causes film 15 to sag until it touches the surface of layer 19.

The spring forces of two helical springs 4 and 10 are dimensioned such that when added together they overcome the inherent tension of film or foil 15 and only a small load pressure acts on layer 19 to be measured.

The much larger radius of curvature of sagging film or foil 15 with which it lies on layer 19 compared to the typical radius of curvature of measurement pole 13, and the lower load pressure of film or foil 15 on layer 19 compared to the load pressure of conventional probes yield a considerable pressure reduction.

Figure 3:
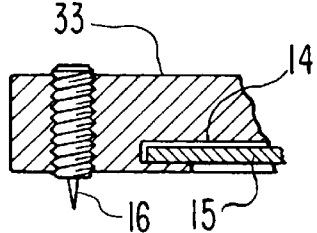
FIG. 3 shows cutout III from FIG. 1 in an enlarged partial representation.
Figure 6:
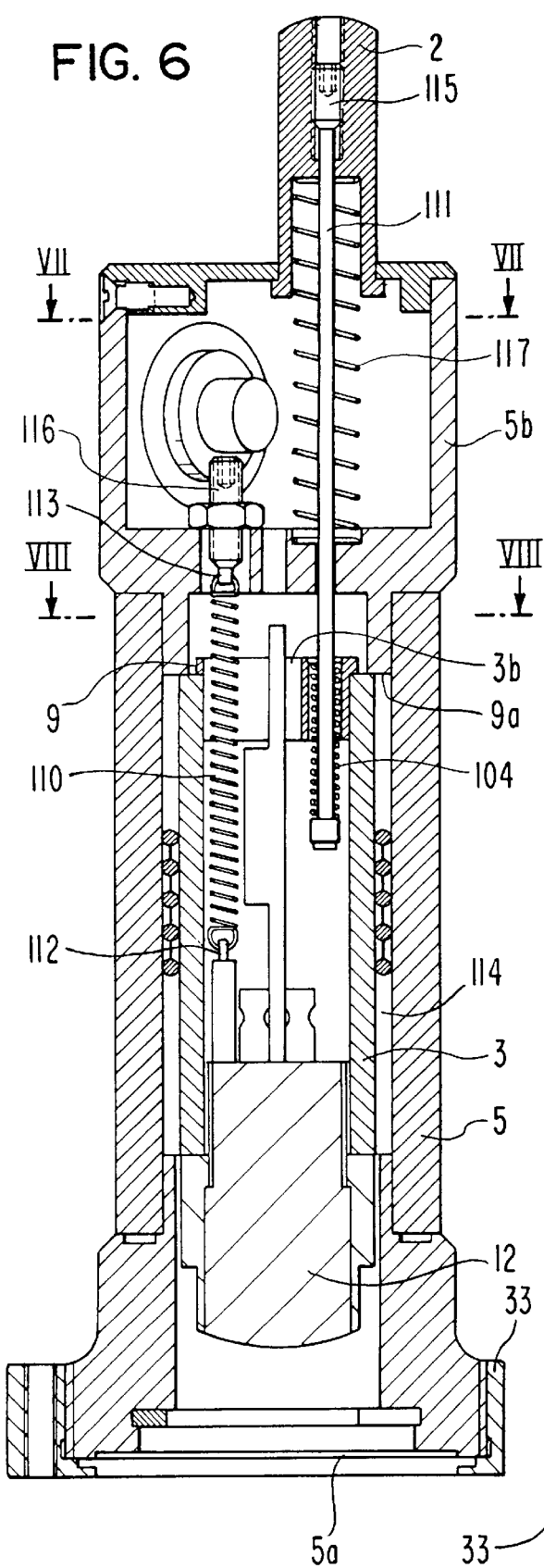
FIG. 6 shows another longitudinal section through another improved version of this measurement probe.
Figure 7:
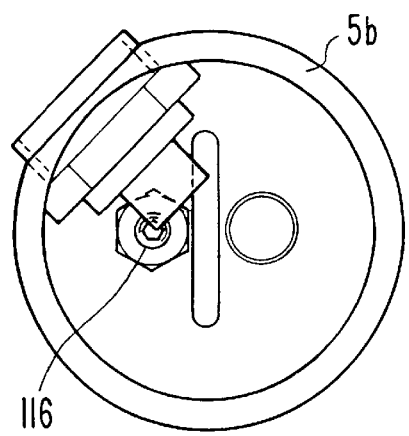
FIG. 7 shows a first section through this probe according to intersection line VII—VII from FIG. 6.

Otherwise the measurement probe of FIGS. 4 and 5 also operates as described above using the embodiments of FIGS. 1 through 3. The same parts are provided with the same reference numbers as there. Instead of compression springs, helical springs 4, 10 can also optionally be used in the form of tension springs.

The latter is the case in the third embodiment of FIGS. 6 through 8 or 9. In this measurement probe the two helical springs are made as tension springs. Here weaker tension spring 104 is located between sliding element 2 and guide means 3 with measurement sensor 12 and other stronger tension spring 110 is located between guide means 3 and housing head 5b.

Two tension springs 104, 110 are located next to one another in the interior of the guide tube used as guide means 3 parallel to its axis. On its upper end weaker tension spring 104 is joined to upper crosspiece 3b inserted by force- and form-fit into the guide tube and with its lower end is attached to adjustment pin 111 which penetrates springs 104 over the full length from the top; on the upper end of the pin sliding element 2 or the pusher sits on the housing top. Other stronger tension spring 110 is clamped between retaining eye 112 in guide tube 3 above measurement sensor 12 and adjustable retaining eye 113 on housing head 5b.

Tubular guide means 3 is guided especially easily in probe housing 5 with ball guide 114. In this way two tension springs 104, 110 can be matched exactly to one another to achieve low load pressures.

Figure 8:
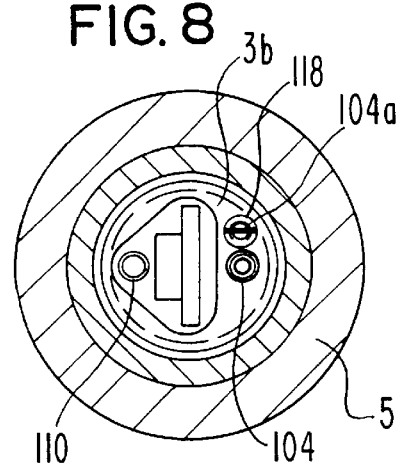
FIG. 8 shows a second section according to intersection line VIII—VIII.

Adjustment pin 111 for weaker tension spring 104 is attached to be adjustable in length from the outside to sliding element 2 or the pusher by means of upper threaded head 115. Upper spring end 104a of this tension spring 104 is hinged laterally, as shown in FIG. 8, and is attached to crosspiece 3b by retaining screw 118.

Upper retaining eye 113 for stronger tension spring 110 is thus part of set screw 116 which is attached to be adjustable lengthwise in housing head 5b above guide means 3.

In addition, sliding element 2 in housing head 5b is supported by means of additional weak compression spring 117 which produces only a slight finger pressure when measurement sensor 12 is actuated, but has no effect on the function of the two tension springs.

As in the other two embodiments, in this measurement probe the measurement pole, when it touches the surface to be measured, first has zero load pressure, and it then increases linearly to an adjustable boundary value. The boundary value can be set by the operator from zero Newtons to a few hundredths of a Newton.

By fixing the measurement probe in the measurement position on the surface of the measurement article and by pressing the sliding element again, as a result of precise guidance of the sensor system in the housing arrangement, pinpoint reset of the measurement sensor on the surface of the measurement article is ensured.

The tension springs which are almost of the same strength depending on design, thus, interact with one another such that only the difference pressure acts as the load pressure of the measurement pole, regardless of how strongly the probe housing is pressed onto the surface and how strongly the sliding element or the pusher is pressed into the probe housing. The difference pressure can also be zero in an extreme case. The load pressure is independent of layer thickness.

Figure 9:
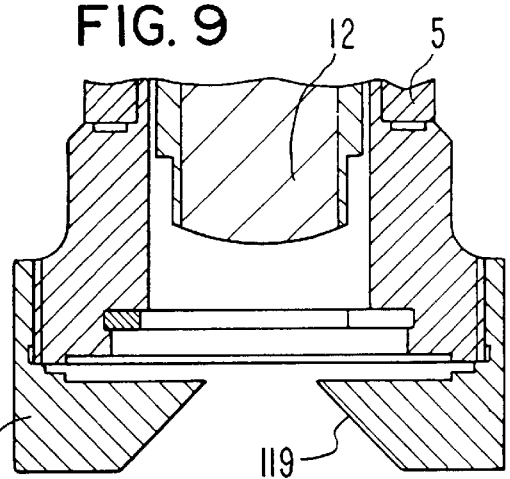
FIG. 9 shows a section through the probe foot with inverted V-shaped notch or groove for measurement on articles arched lengthwise.

Guide means 3 can be made as a tube, plunger, rod, ball guide or in some other suitable form without departing from the framework of the invention. Likewise all embodiments of the measurement probe shown can also be provided with screw-off probe foot 33 which, as is shown in FIG. 9, has an inverted V-shaped notch or groove 119 for measurement on articles which are arched lengthwise.

Reference Number List
1 measurement probe
2 sliding element or pusher
2a grip cap
2b press pin
3 guide means
3a thread
3b crosspiece
4 helical spring
5 probe housing
5b housing head
5a opening
6 carrier pin
6a carrier pin
7 support ring
8 longitudinal slot
8a longitudinal slot
9 stop
9a abutment
10 helical spring
11 lead wires
12 measurement sensor
13 measurement pole
14 annular groove
15 pressure reduction film or foil
16 seating tip
17 antikink measure
18 probe cable
19 layer
20 base material
30 abutment
31 spacer ring
32 spacer ring
33 probe foot
33a bottom
34 screw thread
35 annular nut
36 thread
37 opening
38 annular flange
39 recess
40 longitudinal slot
40a longitudinal slot
41 stud
42 thread
43 annular nut
44 scale
45 circuit board
50 damping system
104 tension spring
104a a upper spring end
110 tension spring
111 adjustment pin
112 retaining eye
113 retaining eye
114 ball guide
115 threaded head
116 set screw
117 compression spring
118 retaining screw
119 notch or V-groove

What is claimed is:

1. A measurement probe for measuring thin layers on a base material using a magnetic or eddy current process with tubular probe housing (5) with face-side lower opening (5a) for measurement sensor (12) with measurement pole (13) which is located on the bottom end of guide means (3) which is guided to move in the longitudinal axis of probe housing (5) against spring action as limited by a stop, in the initial position or rest position of measurement sensor (12) stop (9) on guide means (3) interacting with abutment (9a) on the probe housing, characterized in that above abutment (9a) sliding element (2) for measurement sensor (12) is guided to move on probe housing (5) as limited by a stop, and that in the path of the force between sliding element (2) and measurement sensor (12) there are two interacting helical springs (4, 10) with differing spring force which are dimensioned such that in the initial position of measurement sensor (12) the spring force of one helical spring (4) is less than the spring force of other helical spring (10), such that when sliding element (2) is actuated first one helical spring (4) is tensioned until its spring force overcomes the opposing force of other helical spring (10) and in this way guide means (3) with measurement sensor (12) is moved first against the action of other helical spring (10) from the withdrawn rest position into the measurement position, after the latter being reached further pressure on sliding element (2) is elastically captured by the first helical spring (4).

2. The measurement probe as claimed in claim 1, wherein helical springs (4, 10) are made as compression springs and are located coaxially behind one another on guide means (3).

3. The measurement probe as claimed in claim 2, wherein first helical compression spring (4) is located between sliding element (2) and adjustable stop (9) on guide means (3), and wherein second helical compression spring (10) is clamped between adjustable stop (9) on guide means (3) and lower abutment (30) on probe housing (5) and guide means (3) with measurement sensor (12) in the rest state presses against abutment (9a) on probe housing (5), measurement sensor (12) assuming a distance from opening (5a) on probe housing (5) which corresponds to the spring path of second helical compression spring (10) when sliding element (2) is actuated for a measurement process.

4. The measurement probe as claimed in claim 3, wherein stop (9) for helical springs (4, 10) is axially adjustable on guide means (3).

5. The measurement probe as claimed in claim 4, wherein stop (9) for two helical springs (4, 10) is an annular nut which is adjustable on guide means (3) in thread (3a).

6. The measurement probe as claimed in claim 5, wherein on guide means (3), on the end of helical springs (4, 10) there are one or more spacer rings (31, 32) for setting the final load pressure of measurement pole (13) on layer (19) to be measured.

7. The measurement probe as claimed in claim 6, wherein probe housing (5) has probe foot (33) which is flared in the manner of a flange around opening (5a) for measurement sensor (12).

8. The measurement probe as claimed in claim 7, wherein probe foot (33) is detachably joined to the lower part of probe housing (5) by means of screw thread (34) or a quarter-turn connection.

9. The measurement probe as claimed in claim 8, wherein probe foot (33) consists of transparent acrylic glass.

10. The measurement probe as claimed in claim 9, wherein sliding element (2) for measurement sensor (12) is made as cylindrical grip cap (2a) which extends over the top end of probe housing (5), with two carrier pins (6, 6a) which are pointed radially to the inside and which are guided in longitudinal slots (8, 8a) parallel opposite one another on probe housing (5) on either side of guide means (3) as limited by stops, and rest with their free ends on support ring (7) as the upper abutment for first helical spring (4).

11. The measurement probe as claimed in claim 10, wherein on probe housing (5) there is axially adjustable annular nut (35) as the lower end stop for grip cap (2a).

12. The measurement probe as claimed in claim 9, wherein sliding element (2) for measurement sensor (12) is made as tubular press pin (2b) which is arranged to move in the manner of a telescope and limited by a stop on the top end of guide means (3) and in concentric opening (37) on the top end of probe housing (5) and with its lower annular end it is used as an abutment for upper helical spring (4).

13. The measurement probe as claimed in claim 12, wherein press pin (2b) on the bottom end has annular flange (38) with which it is axially supported on inner recess (39) on the top end of probe housing (5).

14. The measurement probe as claimed in claim 13, wherein press pin (2b) has longitudinal slot (40) and guide means (3) has longitudinal slot (40a) for stud (41) which projects to the inside from probe housing for locking purposes.

15. The measurement probe as claimed in claim 13, wherein on press pin (2b) there is annular nut (43) with scale (44) for preselectable adjustment of the final load pressure on the measurement article by limiting the path when actuation element or pusher (2) is pressed down.

16. The measurement probe as claimed in claim 15, wherein on the upper end of measurement probe (1) probe cable (18) proceeds from grip cap (2a) or press pin (2b) and inside of measurement probe (1) by means of flexible lead wires (11) is joined to circuit board (45) which is located within guide means (3) for measurement sensor (12) and which is connected to measurement sensor (12).

17. The measurement probe as claimed in one of claim 16, wherein on probe foot (33) around opening (5a) for measurement sensor (5) there are at least three seating tips (16).

18. The measurement probe as claimed in one of claim 17, wherein in opening (5a) for measurement sensor (12) film or foil (15) for pressure reduction is attached to probe foot (33).

19. The measurement probe as claimed in claim 18, wherein film or foil (15) for pressure reduction consists of elastic, dimensionally stable material such as plastic or bronze, of such a composition that powdery layer materials for the most part do not adhere to ft.

20. The measurement probe as claimed in claim 18, wherein film or foil (15) for pressure reduction is located in the manner of a membrane on its periphery in annular groove (14) on probe housing (5) or on probe foot (33).

21. The measurement probe as claimed in claim 18, wherein film or foil (15) has a corrugated external area.

22. The measurement probe as claimed in claim 21, wherein between actuation element (2) and measurement sensor (12) there is pneumatic or hydraulic damping system (50) which, regardless of the actuation speed, for the most part allows measurement sensor (12) to be lowered by hand with a uniform, but slow speed against film or foil (15) and layer (19) to be measured.

23. The measurement probe as claimed in claim 1, wherein at least one of two helical springs (4, 10) is made as a compression spring.

24. The measurement probe as claimed in claim 1, wherein two helical springs (4, 10) are made as tension springs, weaker tension spring (104) being located between sliding element (2) and guide means (3) with measurement sensor (12) and other stronger tension spring (110) being located between guide means (3) and housing head (5b).

25. The measurement probe as claimed in claim 24, wherein two tension springs (104, 110) are located next to one another in the interior of guide means (3) parallel to its axis, on its upper end weaker tension spring (104) being joined to upper crosspiece (3b) on guide means (3) and with its lower end its being attached to adjustment pin (111) which penetrates springs (104) over the full length from the top, on its upper end sliding element (2) or the pusher sitting on the housing top, and wherein other stronger tension spring (110) is clamped between retaining eye (112) within guide means (3) above measurement sensor (12) and adjustable retaining eye (113) on housing head (5b).

26. The measurement probe as claimed in claim 25, wherein guide means (3) is guided in probe housing (5) with ball guide (114).

27. The measurement probe as claimed in claim 26, wherein adjustment pin (111) for weaker tension spring (104) is attached to be adjustable in length from the outside to sliding element (2) or the pusher by means of upper threaded head (115).

28. The measurement probe as claimed in claim 27, wherein upper retaining eye (113) for stronger tension spring (110) is part of set screw (116) which is attached to be adjustable lengthwise in housing head (5b) above guide means (3).

29. The measurement probe as claimed in claim 28, wherein sliding element (2) in housing head (5b) is supported by means of additional weak compression spring (117) which produces only a slight finger pressure when measurement sensor (12) is actuated, but has no effect on the function of the two tension springs.

30. The measurement probe as claimed in claim 1, wherein first helical compression spring (4) is located between sliding element (2) and adjustable stop (9) on guide means (3), and wherein second helical compression spring (10) is clamped between adjustable stop (9) on guide means (3) and lower abutment (30) on probe housing (5) and guide means (3) with measurement sensor (12) in the rest state presses against abutment (9a) on probe housing (5), measurement sensor (12) assuming a distance from opening (5a) on probe housing (5) which corresponds to the spring path of second helical compression spring (10) when sliding element (2) is actuated for a measurement process.

31. The measurement probe as claimed in claim 1, wherein stop (9) for helical springs (4, 10) is axially adjustable on guide means (3).

32. The measurement probe as claimed in claim 1, wherein stop (9) for two helical springs (4, 10) is an annular nut which is adjustable on guide means (3) in thread (3a).

33. The measurement probe as claimed in claim 1, wherein on guide means (3), on the end of helical springs (4, 10) there are one or more spacer rings (31, 32) for setting the final load pressure of measurement pole (13) on layer (19) to be measured.

34. The measurement probe as claimed in claim 1, wherein probe housing (5) has probe foot (33) which is flared in the manner of a flange around opening (5a) for measurement sensor (12).

35. The measurement probe as claimed in claim 1, wherein sliding element (2) for measurement sensor (12) is made as cylindrical grip cap (2a) which extends over the top end of probe housing (5), with two carrier pins (6, 6a) which are pointed radially to the inside and which are guided in longitudinal slots (8, 8a) parallel opposite one another on probe housing (5) on either side of guide means (3) as limited by stops, and rest with their free ends on support ring (7) as the upper abutment for first helical spring (4).

36. The measurement probe as claimed in claim 1, wherein sliding element (2) for measurement sensor (12) is made as tubular press pin (2b) which is arranged to move in the manner of a telescope and limited by a stop on the top end of guide means (3) and in concentric opening (37) on the top end of probe housing (5) and with its lower annular end it is used as an abutment for upper helical spring (4).

37. The measurement probe as claimed in claim 1, wherein on the upper end of measurement probe (1) probe cable (18) proceeds from grip cap (2a) or press pin (2b) and inside of measurement probe (1) by means of flexible lead wires (11) is joined to circuit board (45) which is located within guide means (3) for measurement sensor (12) and which is connected to measurement sensor (12).

38. The measurement probe as claimed in one of claim 1, wherein on probe foot (33) around opening (5a) for measurement sensor (5) there are at least three seating tips (16).

39. The measurement probe as claimed in one of claim 1, wherein in opening (5a) for measurement sensor (12) film or foil (15) for pressure reduction is attached to probe foot (33).

40. The measurement probe as claimed in claim 1, wherein between actuation element (2) and measurement sensor (12) there is pneumatic or hydraulic damping system (50) which, regardless of the actuation speed, for the most part allows measurement sensor (12) to be lowered by hand with a uniform, but slow speed against film or foil (15) and layer (19) to be measured.

* * * * *